(12) United States Patent
Hubner et al.

(10) Patent No.: US 6,923,646 B2
(45) Date of Patent: Aug. 2, 2005

(54) PROCESS AND APPARATUS FOR TREATING AN EXHAUST STREAM FROM A DENTAL OPERATORY

(75) Inventors: Henry Hubner, Amityville, NY (US); Elliot R. Gemunder, Dix Hills, NY (US); Selwyn Foster, Jr., Laurelton, NY (US)

(73) Assignee: Air Techniques, Inc., Hicksville, NY (US)

( * ) Notice: Subject to any disclaimer, the term of this patent is extended or adjusted under 35 U.S.C. 154(b) by 259 days.

(21) Appl. No.: 10/124,668

(22) Filed: Apr. 17, 2002

(65) Prior Publication Data

US 2003/0198919 A1 Oct. 23, 2003

Related U.S. Application Data

(60) Provisional application No. 60/284,225, filed on Apr. 18, 2001.

(51) Int. Cl.[7] ............................................. A61C 17/06
(52) U.S. Cl. .................................... 433/92; 417/199.2
(58) Field of Search .............................. 433/92, 91, 93, 433/94, 95, 96; 417/199.2

(56) References Cited

U.S. PATENT DOCUMENTS 5,046,478 A * 9/1991 Clawson .................. 126/110 R
5,551,845 A * 9/1996 Milam ........................ 417/290

* cited by examiner

Primary Examiner—John J Wilson
(74) Attorney, Agent, or Firm—Clifford G. Frayne; Louis E. Marn

(57) ABSTRACT

There is disclosed a process and apparatus for withdrawing an exhaust stream including gas, liquids and solids from the dental operatory connected to the suction side of a vacuum pump wherein solids and liquids are sequentially removed such that compressed gas from the vacuum pump is passed through a heat exchanger for cooling, thus permitting the use of lightweight, less expensive conduit piping for a vent exhaust conduit.

1 Claim, 2 Drawing Sheets

PROCESS AND APPARATUS FOR TREATING AN EXHAUST STREAM FROM A DENTAL OPERATORY

RELATED APPLICATIONS

Applicants claim the benefit of provisional application No. 60/284,225 filed Apr. 18, 2001.

BACKGROUND OF THE INVENTION

1. Field of the Invention

This invention relates to a process and apparatus for treating an exhaust stream and more particularly to a process and application for treating an exhaust stream from a dental operatory.

2. Description of the Prior Art

Dental operatories generally utilize a dental exhaust vacuum system to withdraw gas, liquids and solids through a mouth piece inserted into the patient's mouth or expectorated by the patient. Solids are normally collected by a mesh grid positioned in the line and are removed from the flow and collected under the influence of gravity. The residual gas and liquids are then passed through a separation tank which the liquids are collected and are discharged into a sewer. The remaining stream gas is in fluid communication with the suction side of a vacuum pump which provides low pressure for the dental exhaust vacuum system and is thence passed through a conduit for venting to the atmosphere.

The vacuum pump in dental vacuum systems commonly consist of side channel blowers of one or more stages which compress the outlet gas. Depending upon the vacuum being drawn, (i.e. inches of mercury), such compression process can result in a temperature increase of the exhaust stream gas which in some cases may reach 300° F. A temperature level of such magnitude exceed the temperature rating of plastic piping, such as PVC Type 1 or ABS which is used as a common plumbing conduit. In the present state of the art, dental equipment manufacturers recommend the use of metal piping downstream of the vacuum pump to withstand and dissipate heat of the exhaust gas stream. Such requirement increases installation costs of any such dental exhaust vacuum system.

OBJECTS OF THE INVENTION

An object of the present invention is to provide for a dental exhaust vacuum system having heat exchange capabilities.

Another object of the present invention is to provide for a dental exhaust vacuum system having heat exchange capabilities to cool an exhaust gas stream and thus allow the use of less expensive conduit piping.

A still further object of the present invention is to provide for a heat exchanger of an efficient size so as to fit within the support frame of the dental vacuum system.

SUMMARY OF THE INVENTION

There is disclosed a process and apparatus for withdrawing an exhaust stream including gas, liquids and solids from the dental operatory connected to the suction side of a vacuum pump wherein solids and liquids are sequentially removed such that compressed gas from the vacuum pump is passed through a heat exchanger for cooling, thus permitting the use of lightweight, less expensive conduit piping for a vent exhaust conduit.

BRIEF DESCRIPTION OF THE DRAWINGS

Further understanding of the present invention will be had by referring to the accompanying drawings, wherein.

DETAILED DESCRIPTION OF THE DRAWINGS

In a dental operatory, the patient is positioned in a dental chair. While work is proceeding within the oral cavity, fluids and solids are removed from the oral cavity under a vacuum through a mouth piece. This mouth piece is in conduit communication with a vacuum means some distance away. This waste stream, including gas, liquid and solids, is withdrawn and is first introduced into a solid separation zone for removal of the solids, and the residual waste stream is withdrawn further to a fluid separation zone for the removal of fluids so that the final residual air stream consists of air drawn to the vacuum means. It is this vacuum means in the dental exhaust system with which the Applicants have directed their attention with respect to certain problems regarding the temperature of the exhaust air stream.

Figure 1:
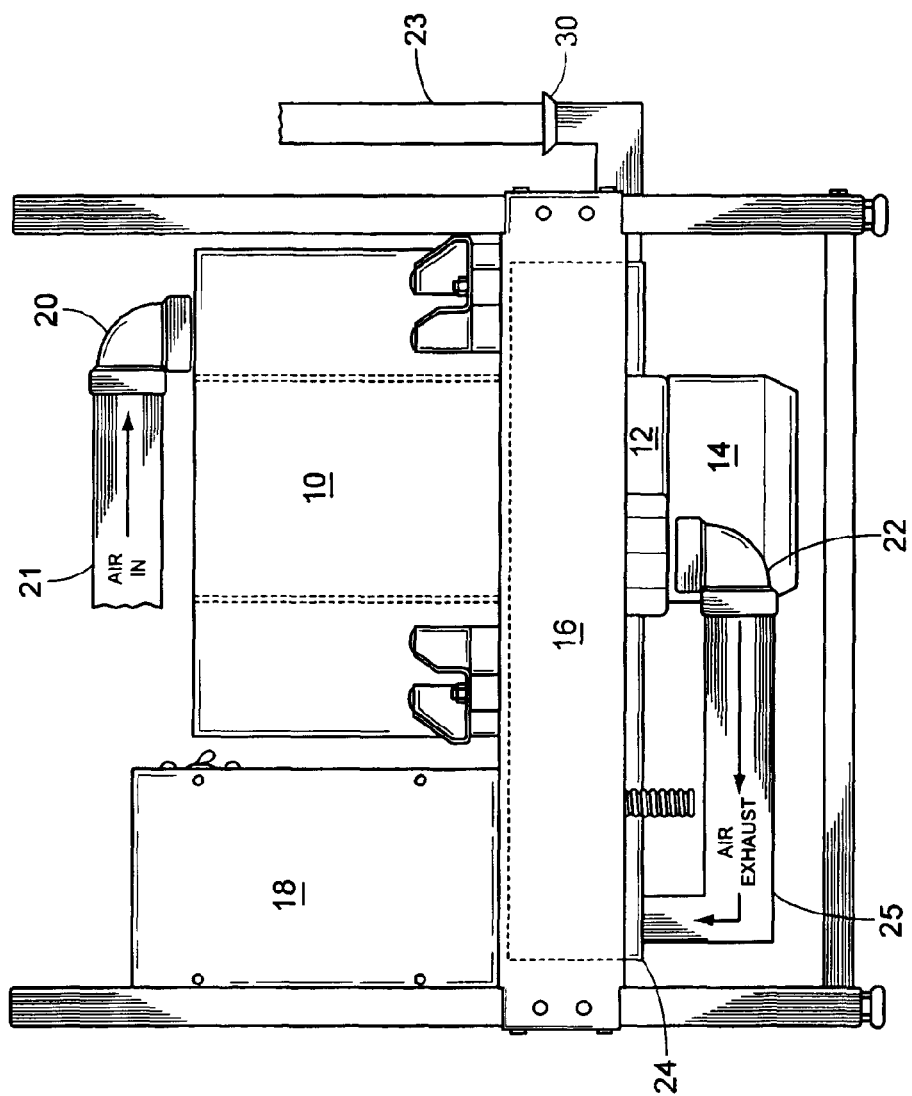
FIG. 1 is a front view of the dental exhaust system of the present invention.
Figure 2:
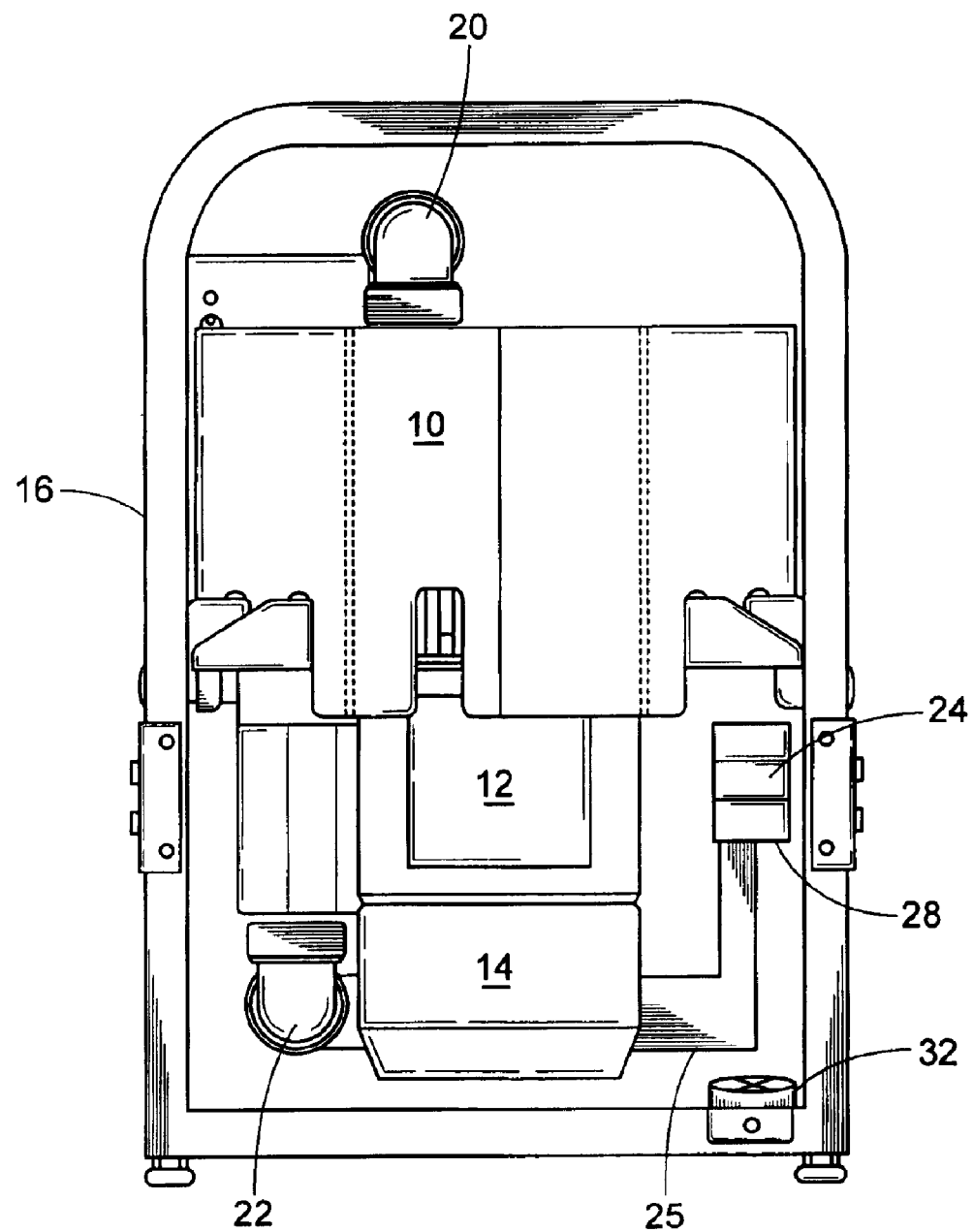
FIG. 2 is a side view of a heat transfer assembly for a dental exhaust system of the present invention.

FIG. 1 is a front view and FIG. 2 is a side view of the vacuum pump portion of a dental vacuum system. In the embodiment illustrated, the vacuum pump 10, its drive motor 12, and cooling fan 14 are securely mounted to a frame 16 which would be positioned somewhere within the dentist's office. Also mounted to the frame 16 is an electrical control panel 18. These elements are mounted to a frame to insure their quietest operation and to prevent vibration regardless of the amount of vacuum being drawn. Typically, these elements are modularly mounted on the frame 16 for convenience and space considerations.

The vacuum pump 10 has an inlet port 20 in communication with conduit 21 for the introduction of air drawn from the operatory which air has had the solids and liquids removed by means of a solids trap and a separation tank in the conduit line (not shown). Vacuum pump 10 has an outlet port 22 for the exhaust air. A conduit 23 is in communication with outlet port 22 to vent the exhaust air to the ambient atmosphere. Depending upon the number of stages in the vacuum pump and the amount of vacuum being drawn, it is these exhaust gases which increase in temperature because of the compression of the vacuum pump and therefore require conduit 23 to be fabricated of metal and to extend from the outlet port 22 to the ambient atmosphere.

Applicant is able to reduce the amount of metal conduit usage from the outlet port 22, to the ambient atmosphere by positioning a convective heat exchanger 24 within the boundaries of frame 16 so that the exhaust air exiting outlet port 22 is sufficiently cooled so as to permit the use of PVC or ABS pipe for conduit 23 to vent to the ambient atmosphere. This is achieved by positioning a metal conduit 25 from exhaust port 22 in communication with heat exchanger 26. Heat exchanger 26 consists of metal enclosure member 28 having a plurality of baffle (not shown) positioned therein. A metal exhaust conduit 25 then exits heat exchanger 24 and terminates with coupling 30 to a PVC or ABS exhaust conduit 23 which then vents the exhaust gases to the ambient atmosphere.

Depending upon the temperature of the exhaust gases from the vacuum pump 10, sufficient heat may be dissipated by passive convection from the enclosure member 28 to the surrounding air. Additionally, dissipation of heat could be accomplished by active convection utilizing the drive motor cooling fan 14 which cools the drive motor of the vacuum pump 10. Still further, active convection to dissipate heat could be encouraged by positioning an auxiliary fan 32 on frame 16 so as to direct air over and around enclosure member 28. The temperature of the exhaust gases are therefore reduced sufficiently that ABS or PVC pipe may be used for conduit 23.

While it will be recognized by those of ordinary skill in the art that many modifications or changes may be made to the invention as disclosed, it is manifestly intended that the invention be limited only by the claims and the equivalence thereof.

We claim:

1. Apparatus for treating a waste stream from a dental operatory which comprises:

means for compressing a gaseous waste stream from a dental operatory, said means for compressing having a suction inlet port and a compressed gas outlet port;

conduit means for withdrawing said gaseous waste stream from said dental operatory said conduit means in fluid communication with said suction inlet port of said means for compressing a gaseous waste stream;

heat exchanger means including an inlet port and an outlet port for cooling said gaseous waste stream;

conduit means in fluid communication with said compressed gas outlet port of said means for compressing a gaseous waste stream and said inlet port of said heat exchanger means;

conduit means for venting to atmosphere said gaseous waste stream exiting said outlet port of said heat exchanger means, said conduit means for venting to atmosphere comprising polymer pipe.

* * * * *